United States Patent

[19]

Matsunaga et al.

[11] Patent Number: 5,808,087
[45] Date of Patent: Sep. 15, 1998

[54] SULFONIUM SALTS OF PYRROLYLBENZIMIDAZOLES

[75] Inventors: Akio Matsunaga; Yuki Mita; Hiroshi Kohno; Hajime Edatsugi; Daiji Iwata, all of Chiba-ken, Japan

[73] Assignee: Mitsui Chemicals, Inc., Tokyo, Japan

[21] Appl. No.: 753,435

[22] Filed: Nov. 25, 1996

[30] Foreign Application Priority Data

Nov. 29, 1995 [JP] Japan .................................. 7-310729

[51] Int. Cl.$^6$ ........................ C07D 403/02; A61K 31/415
[52] U.S. Cl. .................................. 548/306.1; 514/394
[58] Field of Search ..................... 548/306.1; 514/394

[56] References Cited

U.S. PATENT DOCUMENTS

| | | | |
|---|---|---|---|
| 2,689,853 | 9/1954 | Schenck et al. | 548/306.1 |
| 3,155,571 | 11/1964 | Sarett et al. | 548/306.1 X |
| 3,309,378 | 3/1967 | Dunn | 548/306.1 X |
| 3,325,506 | 6/1967 | Jones et al. | 548/306.1 X |
| 5,273,991 | 12/1993 | Lee | 514/397 |

FOREIGN PATENT DOCUMENTS

| | | | |
|---|---|---|---|
| 0246868 | 11/1987 | European Pat. Off. | |
| 0711768 | 5/1996 | European Pat. Off. | |
| 1117000 | 11/1961 | Germany | 548/306.1 |
| 49-5967 | 1/1974 | Japan | 548/306.1 |
| 52-5769 | 1/1977 | Japan | 548/306.1 |
| 0583226 | 12/1976 | Switzerland | 548/306.1 |
| WO93/13739 | 7/1993 | WIPO | |

OTHER PUBLICATIONS

Arcamone et al, "Synthesis, DNA–Binding Properties, and Antitumor Activity of Novel Distamycin Derivatives", *J. Med. Chem.*, 1989, 32, pp. 774–778.

Alley et al, "Feasibility of Drug Screening with Panels of Human Tumor Cell Lines Using a Microculture Tetrazolium Assay", *Cancer Research*, 1988, 48, pp. 589–601.

Arcamone et al, "Structure and Synthesis of Distamycin A", *Nature*, 1964, vol. 203, pp. 1064–1065.

Baker et al, "Sequence–Specific Cleavage of Double–Helical DNA. N–Bromoacetyldistamycin", *J. Am. Chem. Soc.*, 1985, 107, pp. 8266–6268.

*Primary Examiner*—Floyd D. Higel
*Attorney, Agent, or Firm*—Burns, Doane, Swecker and Mathis, L.L.P.

[57] ABSTRACT

Compounds of formula (1):

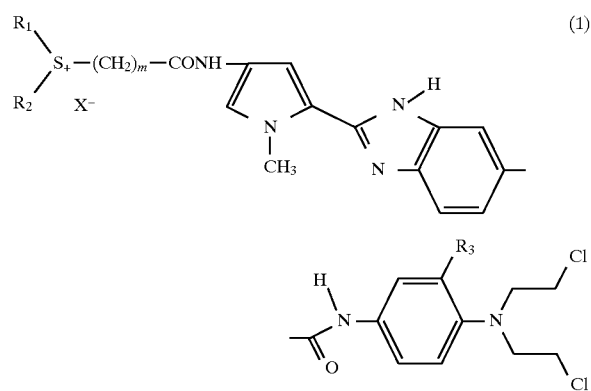

wherein m is an integer 1, 2 or 3, $R_1$ and $R_2$ are the same or independently different alkyl groups, each having 1–5 carbon atoms, $R_3$ is a hydrogen atom, alkyl group having 1–3 carbon atoms, alkoxy group having 1–3 carbon atoms or halogen atom, and $X^-$ is an acid residue of acid selected from a group consisting of methanesulfonic acid, benzenesulfonic acid, toluenesulfonic acid and trifluoromethanesulfonic acid, and their salts are useful as an effective component of anticancer agents.

10 Claims, No Drawings

SULFONIUM SALTS OF PYRROLYLBENZIMIDAZOLES

BACKGROUND OF THE INVENTION

1. Field of the Invention

The present invention relates to novel benzimidazole derivatives which bind to DNA and suppress growth of cells, to pharmaceutical compositions containing said derivatives, and more specifically to the use of said derivatives in antitumor agents.

2. Description of the Related Art

Some certain compounds which act on DNA are used as antitumor agents. For example, adriamycin is useful as an antitumor agent which is intercalated into DNA. Also, compounds which react with DNA, such as cisplatin and mitomycin, are often used as antitumor agents. The mechanism of such an antitumor activity due to the action on DNA may not be fully understood, but the activity is considered to be generally accepted. On the other hand, distamycin and netropsin have recently become known to bind to DNA and to exhibit an antitumor activity (Nature 203, 1064–65, 1964). These compounds attract attention as a groove binder in which the mode of DNA binding is different from that of conventional antitumor agents.

Nevertheless, based on the knowledge on antitumor agents so far available, it is so far absolutely impossible to predict which partial structures in the compounds are essential or what kind of alternative partial structure can be used regarding the interaction with DNA. However, it is significant to predict the presence of other compounds having desirable structures, and to search for them. Such searches for the new structures are considered to be particularly necessary for the production of novel antitumor agents.

Furthermore, compounds in which an alkylating agent is bound to a distamycin derivative are known. Typical examples are found in J. Am. Chem. Soc. 107, 8266, 1985; EP 246868; WO 93-13739; J. Med. Chem. 32, 774, 1989, etc. A compound similar to distamycin, in which partial structures, N-methylimidazole residues, are linked via amide bonds, having a binding alkylating agent are also known (U.S. Pat. No. 5,273,991). In some of these compounds, a bis(2-chloroethyl)amino residue, which is now known as a part of a structure of an antitumor agent, is used as an alkylating agent. For example, chlorambucil is known as an antitumor agent which has a bis(2-chloroethyl) amino residue in the molecule. The antitumor activity of this compound is suggested to be a result of alkylation of DNA, enzymes or the like. However, to date, there is no clear data to show the significance of the addition of an alkylating agent having a chloroethylamine structure as a part of a DNA-binding antitumor agent.

SUMMARY OF THE INVENTION

An object of the present invention is to provide a novel compound which acts on DNA or has a partial structure which acts on DNA and is effective as an antitumor agent.

The above-mentioned distamycin is a typical compound which binds to DNA. Distamycin is characterized by its structure in which aromatic pyrrole rings are linked via amide bonds. However, DNA-binding structures, associated with their level of effectiveness, do not seem to have been studied. Consequently, the present inventors presumed that there must be a novel compound which has a structure different from those of previously known compounds, while partially retaining its pyrrole group in the structure, and yet shows an antitumor activity, and thus searched for the new structure.

Further, the present inventors disclosed a group of compounds, including compounds which have the above-mentioned structure, in the International Patent Application No. PCT/JP/01034 (WO 95/32960; EP Publication No. 0711768A1). After searching particularly for novel compounds in which pyrrole and benzimidazole groups are directly bound and other substituting groups are attached via amide bonds, the present inventors specifically selected a 1H-2-(4-nitropyrrol-2-yl)benzimidazole-5-carboxamide derivative as a compound useful as a partial structure of an antitumor agent. To this compound, an alkylating agent was added, an alkylthio derivative was bound at position 4 of the pyrrole ring, and additional alkyl groups were introduced in its thio group to obtain a sulfonium compound. Study on the effects of this sulfonium compound showed that the compound had a potential to be a highly active antitumor agent. Further, it was also found that a compound which has a sulfonic acid, such as p-toluenesulfonic acid or methanesulfonic acid, as a counter anion of this sulfonium compound has comparatively good stability.

Based on the above-mentioned new findings, the present inventors achieved the invention of novel antitumor agents.

Namely, the present invention comprises the compounds represented by the following formula (1):

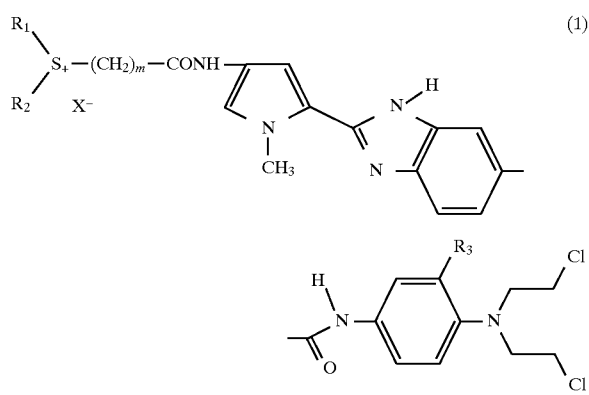

wherein
  m is an integer 1, 2 or 3, $R_1$ and $R_2$ are the same or independently different alkyl groups, each having 1–5 carbon atoms,
  $R_3$ is a hydrogen atom, alkyl group having 1–3 carbon atoms, alkoxy group having 1–3 carbon atoms or halogen atom, and
  $X^-$ is an acid residue of acid selected from the group consisting of methanesulfonic acid, benzenesulfonic acid, toluenesulfonic acid and trifluoromethanesulfonic acid, and salts thereof.

Furthermore, among the compounds of formula (1), compounds in which $R_3$ is a hydrogen atom, methyl group, methoxy group or chlorine atom are preferable, and compounds in which both $R_1$ and $R_2$ are a methyl group are further preferable.

Compounds of formula (1) and pharmaceutically acceptable salts thereof are novel compounds which act on DNA or have a partial structure which acts on DNA and can be used for the preparation of an antitumor agent using the compounds in an effective amount.

DETAILED DESCRIPTION OF THE INVENTION AND PREFERRED EMBODIMENTS

The present invention will be explained more in detail as follows:

A sulfonium group which is substituted with an alkyl group having 1–5 carbon atoms represents a sulfonium group which is substituted with a straight or branched alkyl group having 1–5 carbon atoms, and said substituting alkyl group as $R_1$ and $R_2$ is preferably, for example, a methyl, ethyl, n-propyl, i-propyl, n-butyl, i-butyl, t-butyl or n-pentyl group.

An alkyl group having 1–3 carbon atoms as $R_3$ is preferably a methyl, ethyl, n-propyl or i-propyl group.

An alkoxy group having 1–3 carbon atoms as $R_3$ is preferably a methoxy, ethoxy, n-propyloxy or i-propyloxy group.

A halogen atom as $R_3$ represents a fluorine, chlorine, bromine or iodine atom.

Examples of salts of these compounds include their salts with an inorganic acid such as sulfuric acid, nitric acid or phosphoric acids and their salts with an organic acid such as methanesulfonic acid, toluenesulfonic acid, trifluoromethanesulfonic acid, benzenesulfonic acid, nitrobenzenesulfonic acid, camphorsulfonic acid, acetic acid, fumaric acid, maleic acid, citric acid, oxalic acid or tartaric acid.

A method of synthesizing these compounds will be explained as follows: In the following description and Examples, DCC represents N,N'-dicyclohexylcarbodiimide, CDI represents N,N'-carbonyldiimidazole, EDCI represents 1-(3-dimethylaminopropyl)-3-ethylcarbodiimide hydrochloride, DECP represents diethylcyanophosphonate, DMF represents dimethylformamide, and THF represents tetrahydrofuran. Pd/C represents palladium-on-charcoal in which a palladium content is generally 5–10% by weight.

Primary intermediates, namely compounds of the following formula (2), can be synthesized according to the method shown in Reference Example 1 hereinafter or the like. These intermediates are described also in Japanese Patent Application 95-154074 (or PCT/JP 95/01034).

Amino compounds of formula (2) can be condensed with carboxylic acid derivatives of formula (3) using a general condensation agent (for example, DCC, CDI, EDCI, DECP) to bind an alkylthio group. Ordinary solvents can be used for these reactions; however, good results can be obtained using DMF or mixed solvents containing DMF. The reaction time is preferably between 30 minutes and 40 hours. The reaction temperature is preferably between 0° and 40° C. Alternatively, compounds of formula (4) can be obtained by using acid chlorides in the same manner. The reaction time in this case is between 1 minute and 1 hour (Reaction Scheme (1)).

Reaction Scheme (1)

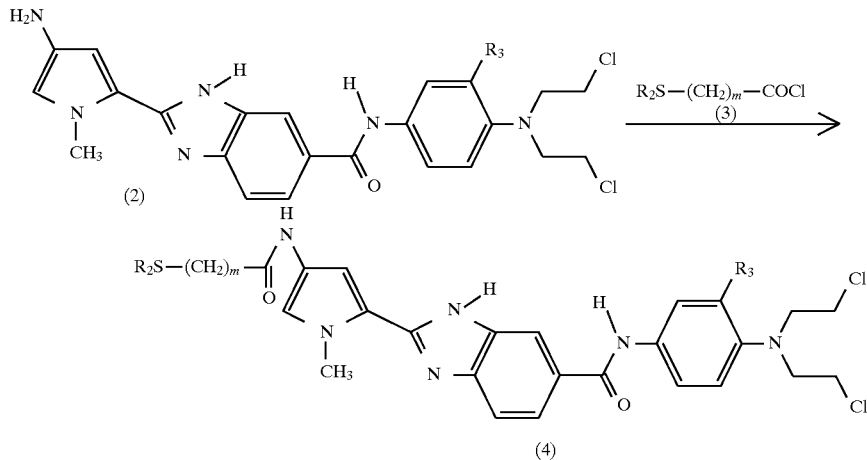

Furthermore, compounds of formula (4) can be alkylated using a sulfonic acid ester such as methyl methanesulfonate, methyl benzenesulfonate, methyl p-toluenesulfonate, ethyl p-toluenesulfonate or propyl p-toluenesulfonate, as an appropriate alkylating agent, to obtain sulfonium derivatives of formula (5). Examples of solvents to be used for this reaction include formic acid, acetic acid, trifluoroacetic acid, hydrobromic acid, methanol, ethanol, isopropanol, butanol, ethyl ether, THF, dioxane, ethyl acetate, acetone, 2-butanone, methylene chloride and chloroform. A mixture of two or more of these solvents can also be used. Alternatively, the reaction can be carried out without a solvent. The reaction time is preferably between 1 and 150 hours. The reaction temperature is preferably between 0° and 60° C. (Reaction Scheme (2)).

acids, methanesulfonic acid, toluenesulfonic acid, camphorsulfonic acid, and the like.

Salts of compounds of formula (4) can be produced by general methods with acids such as methanesulfonic acid, toluenesulfonic acid and camphorsulfonic acid. These salts can be also alkylated in the same manner as shown in Reaction Scheme (2) using a sulfonic acid ester such as methyl methanesulfonate, methyl benzenesulfonate, methyl p-toluenesulfonate, ethyl p-toluenesulfonate, or propyl p-toluenesulfonate, or the like, as an appropriate alkylating agent, to obtain corresponding sulfonium derivatives. Examples of suitable solvents to be used for this reaction include formic acid, acetic acid, trifluoroacetic acid, methanol, ethanol, isopropanol, butanol, ethyl ether, THF, dioxane, ethyl acetate, acetone, 2-butanone, methylene chlo-

Reaction Scheme (2)

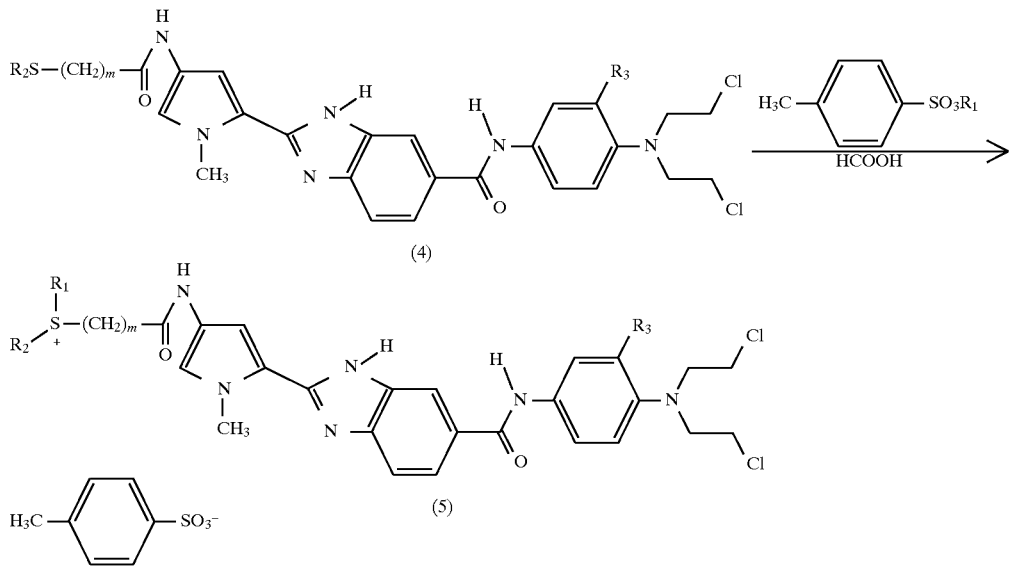

Furthermore, salts of sulfonium derivatives of formula (5) can be produced by general methods with inorganic acids or organic acids such as sulfuric acid, nitric acid, phosphoric ride and chloroform. These solvents can be used either alone or as a mixture of two or more. Alternatively, the reaction can be carried out without a solvent. The reaction time is preferably between 1 and 150 hours. The reaction temperature is preferably between 0° and 60° C. (Reaction Scheme (2)).

Furthermore, corresponding salts can be formed by adding methanesulfonic acid, toluenesulfonic acid or camphorsulfonic acid to the reaction mixture in an amount of 1- to 2-equivalents, by mole, of the compounds of formula (4), when sulfonium derivatives of formula (5) are obtained by alkylating the compounds of formula (4) using a sulfonic acid ester such as methyl methanesulfonate, methyl benzenesulfonate, methyl p-toluenesulfonate, ethyl p-toluenesulfonate or propyl p-toluenesulfonate, as an appropriate alkylating agent. Examples of suitable solvents to be used in this reaction include formic acid, acetic acid, trifluoroacetic acid, methanol, ethanol, isopropanol, butanol, ethyl ether, THF, dioxane, ethyl acetate, acetone, 2-butanone, methylene chloride and chloroform. They can be used either alone or as a mixture of two or more. Alternatively, the reaction can be carried out without a solvent. The reaction time is preferably between 1 and 150 hours. The reaction temperature is preferably between 0° and 60° C.

In general, there are very few examples of usage of compounds having a sulfonium group as pharmaceutical preparations and usage of sulfonic acids as a counterion of these compounds, and there are almost no examples of mold of such compounds particularly in antitumor agents.

Further, the present inventors investigated the stability of these compounds. For this purpose, a test was carried out as follows: An original form of each compound was stored in an incubator at 50° to 60° C. under the conditions that moisture from outside did not affect the compound, and then the remaining rate was measured using HPLC. As a result, it was found that compounds having a counter anion of methanesulfonic acid or p-toluenesulfonic acid were more stable than those having a counter anion of iodine.

However, when the compounds were stored in a refrigerator at about 0°–5° C., the difference in their stability was not significant.

These results show that compounds having a counter anion of methanesulfonic acid or p-toluenesulfonic acid are more stable than compounds having a counter anion of iodine and, therefore, advantageously easy to handle.

Examples of compounds of formula (1) of the present invention are shown in Table 1. In this Table, methanesulfonic acid and toluenesulfonic acid are shown as examples for counter anions for a sulfonium group, but, as mentioned above, the counter anions are not limited to these two groups. When other counter anions have to be specified, a detailed description will be given.

As to the compounds in Table 1, as understood from the structures of the compounds, salts can be formed with moieties other than counter anions. Methods for synthesizing the salts were described above. In the case where a counter anion and an acid residue shown as an alternative moiety of salts are different, the two are not always distinguishable and the ratio is not necessarily 1:1. However, here, both forms of the salts are implicatively included. Examples of sulfonium compounds of the present invention are listed below along with their salt forms. Names of the compounds are expediently given assuming that salts can be newly formed in addition to already existing salts of sulfonium compounds. Because of the above-mentioned reasons, contained acid residues are obviously not fixed.

2-[N-[1-methyl-2-[5-[N-[4-[N,N-bis(2-chloroethyl)amino] phenyl]]carbamoyl]-1H-benzimidazol-2-yl]pyrrol-4-yl] carbamoylethyl-dimethylsulfonium methanesulfonate;

2-[N-[1-methyl-2-[5-[N-[4-[N,N-bis(2-chloroethyl)amino] phenyl]]carbamoyl]-1H-benzimidazol-2-yl]pyrrol-4-yl] carbamoylethyl-dimethylsulfonium methanesulfonate, methanesulfonate;

2-[N-[1-methyl-2-[5-[N-[4-[N,N-bis(2-chloroethyl)amino] phenyl]]carbamoyl]-1H-benzimidazol-2-yl]pyrrol-4-yl] carbamoylethyl-dimethylsulfonium methanesulfonate, p-toluenesulfonate;

2-[N-[1-methyl-2-[5-[N-[4-[N,N-bis(2-chloroethyl)amino] phenyl]]carbamoyl]-1H-benzimidazol-2-yl]pyrrol-4-yl] carbamoylethyl-dimethylsulfonium methanesulfonate, benzenesulfonate;

2-[N-[1methyl-2-[5-[N-[4-[N,N-bis(2-chloroethyl)amino] phenyl]]carbamoyl]-1H-benzimidazol-2-yl]pyrrol-4-yl] carbamoylethyl-dimethylsulfonium p-toluenesulfonate;

2-[N-[1-methyl-2-[5-[N-[4-[N,N-bis(2-chloroethyl)amino] phenyl]]carbamoyl]-1H-benzimidazol-2-yl]pyrrol-4-yl] carbamoylethyl-dimethylsulfonium p-toluenesulfonate, methanesulfonate;

2-[N-[1-methyl-2-[5-[N-[4-[N,N-bis(2-chloroethyl)amino] phenyl]]carbamoyl]-1H-benzimidazol-2-yl]pyrrol-4-yl] carbamoylethyl-dimethylsulfonium p-toluenesulfonate, p-toluenesulfonate;

2-[N-[1-methyl-2-[5-[N-[4-[N,N-bis(2-chloroethyl)amino] phenyl]]carbamoyl]-1H-benzimidazol-2-yl]pyrrol-4-yl] carbamoylethyl-dimethylsulfonium p-toluenesulfonate, benzenesulfonate;

2-[N-[1-methyl-2-[5-[N-[4-[N,N-bis(2-chloroethyl)amino] phenyl]]carbamoyl]-1H-benzimidazol-2-yl]pyrrol-4-yl] carbamoylethyl-dimethylsulfonium benzenesulfonate;

2-[N-[1-methyl-2-[5-[N-[4-[N,N-bis(2-chloroethyl)amino] phenyl]]carbamoyl]-1H-benzimidazol-2-yl]pyrrole-4-yl] carbamoylethyl-dimethylsulfonium benzenesulfonate, methanesulfonate;

2-[N-[1-methyl-2-[5-[N-[4-[N,N-bis(2-chloroethyl)amino] phenyl]]carbamoyl]-1H-benzimidazol-2-yl]pyrrole-4-yl] carbamoylethyl-dimethylsulfonium benzenesulfonate, p-toluenesulfonate;

2-[N-[1-methyl-2-[5-[N-[4-[N,N-bis(2-chloroethyl)amino] phenyl]]carbamoyl]-1H-benzimidazol-2-yl]pyrrole-4-yl] carbamoylethyl-dimethylsulfonium benzenesulfonate, benzenesulfonate;

2-[N-[1-methyl-2-[5-[N-[4-[N,N-bis(2-chloroethyl)amino] phenyl]]carbamoyl]-1H-benzimidazol-2-yl]pyrrole-4-yl] carbamoylethyl-dimethylsulfonium trifluoromethanesulfonate;

2-[N-[1-methyl-2-[5-[N-[4-[N,N-bis(2-chloroethyl)amino] phenyl]]carbamoyl]-1H-benzimidazol-2-yl]pyrrol-4-yl] c a r b a m o y l e t h y l - d i m e t h y l s u l f o n i u m trifluoromethanesulfonate, trifluoromethanesulfonate.

Based on the assumptions mentioned above, the formulae of compounds having methanesulfonic acid or toluenesulfonic acid as the counter anion to the sulfonium group are listed in Table 1. Although not shown in this table, it should be understood that examples of other counter anions are also included. Compound numbers in this text correspond to compound numbers in Table 1.

TABLE 1

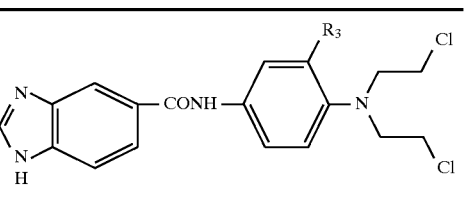

| No. | X⁻ | R₁ | R₂ | R₃ | m |
|---|---|---|---|---|---|
| 1 | $CH_3SO_3-$ | $CH_3$ | $CH_3$ | H | 2 |
| 2 | $CH_3SO_3-$ | $CH_3$ | $CH_3$ | $CH_3$ | 2 |
| 3 | $CH_3SO_3-$ | $CH_3$ | $CH_3$ | Cl | 2 |
| 4 | $CH_3SO_3-$ | $CH_3$ | $CH_3$ | $OCH_3$ | 2 |
| 5 | $CH_3SO_3-$ | $CH_2$ | $CH_3CH_3$ | H | 2 |
| 6 | $CH_3SO_3-$ | $CH_2$ | $CH_3CH_3$ | $CH_3$ | 2 |
| 7 | $CH_3SO_3-$ | $CH_2$ | $CH_3CH_3$ | Cl | 2 |
| 8 | $CH_3SO_3-$ | $CH_2$ | $CH_3CH_3$ | $OCH_3$ | 2 |
| 9 | $CH_3SO_3-$ | $CH_2$ | $CH_3CH_2CH_3$ | H | 2 |
| 10 | $CH_3SO_3-$ | $CH_2$ | $CH_3CH_2CH_3$ | $CH_3$ | 2 |
| 11 | $CH_3SO_3-$ | $CH_2$ | $CH_3CH_2CH_3$ | Cl | 2 |
| 12 | $CH_3SO_3-$ | $CH_2$ | $CH_3CH_2CH_3$ | $OCH_3$ | 2 |
| 13 | $CH_3SO_3-$ | $CH_3CH_2$ | $CH_3CH_2$ | H | 2 |
| 14 | $CH_3SO_3-$ | $CH_3CH_2$ | $CH_3CH_2$ | $CH_3$ | 2 |
| 15 | $CH_3SO_3-$ | $CH_3CH_2$ | $CH_3CH_2$ | Cl | 2 |
| 16 | $CH_3SO_3-$ | $CH_3CH_2$ | $CH_3CH_2$ | $OCH_3$ | 2 |
| 17 | $CH_3SO_3-$ | $CH_3CH_2$ | $CH_3CH_2CH_2$ | H | 2 |
| 18 | $CH_3SO_3-$ | $CH_3CH_2$ | $CH_3CH_2CH_2$ | $CH_3$ | 2 |
| 19 | $CH_3SO_3-$ | $CH_3CH_2$ | $CH_3CH_2CH_2$ | Cl | 2 |
| 20 | $CH_3SO_3-$ | $CH_3CH_2$ | $CH_3CH_2CH_2$ | $OCH_3$ | 2 |
| 21 | $CH_3SO_3-$ | $CH_3CH_2CH_2$ | $CH_3CH_2CH_2$ | H | 2 |
| 22 | $CH_3SO_3-$ | $CH_3CH_2CH_2$ | $CH_3CH_2CH_2$ | $CH_3$ | 2 |
| 23 | $CH_3SO_3-$ | $CH_3CH_2CH_2$ | $CH_3CH_2CH_2$ | Cl | 2 |
| 24 | $CH_3SO_3-$ | $CH_3CH_2CH_2$ | $CH_3CH_2CH_2$ | $OCH_3$ | 2 |
| 25 | 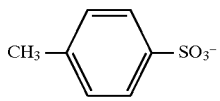 | $CH_3$ | $CH_3$ | H | 2 |
| 26 |  | $CH_3$ | $CH_3$ | $CH_3$ | 2 |
| 27 | 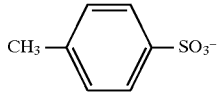 | $CH_3$ | $CH_3$ | Cl | 2 |
| 28 | 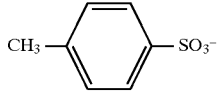 | $CH_3$ | $CH_3$ | $OCH_3$ | 2 |
| 29 |  | $CH_3$ | $CH_3CH_2$ | H | 2 |
| 30 |  | $CH_3$ | $CH_3CH_2$ | $CH_3$ | 2 |
| 31 | 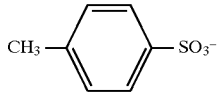 | $CH_3$ | $CH_3CH_2$ | Cl | 2 |
| 32 | 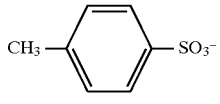 | $CH_3$ | $CH_3CH_2$ | $OCH_3$ | 2 |

TABLE 1-continued
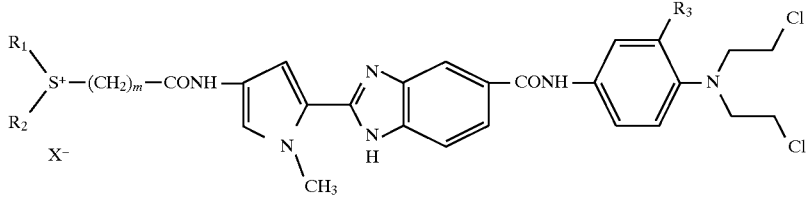
| No. | X⁻ | R₁ | R₂ | R₃ | m |
|---|---|---|---|---|---|
| 33 |  | $CH_3CH_2$ | $CH_3CH_2CH_2$ | H | 2 |
| 34 |  | $CH_3CH_2$ | $CH_3CH_2CH_2$ | $CH_3$ | 2 |
| 35 |  | $CH_3CH_2$ | $CH_3CH_2CH_2$ | Cl | 2 |
| 36 |  | $CH_3CH_2$ | $CH_3CH_2CH_2$ | $OCH_3$ | 2 |
| 37 |  | $CH_3CH_2$ | $CH_3CH_2$ | H | 2 |
| 38 |  | $CH_3CH_2$ | $CH_3CH_2$ | $CH_3$ | 2 |
| 39 |  | $CH_3CH_2$ | $CH_3CH_2$ | Cl | 2 |
| 40 |  | $CH_3CH_2$ | $CH_3CH_2$ | $OCH_3$ | 2 |
| 41 |  | $CH_3CH_2$ | $CH_3CH_2CH_2$ | H | 2 |
| 42 | 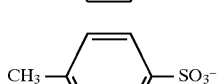 | $CH_3CH_2$ | $CH_3CH_2CH_2$ | $CH_3$ | 2 |
| 43 |  | $CH_3CH_2$ | $CH_3CH_2CH_2$ | Cl | 2 |
| 44 |  | $CH_3CH_2$ | $CH_3CH_2CH_2$ | $OCH_3$ | 2 |

TABLE 1-continued

[Structure: R₁R₂S⁺—(CH₂)ₘ—CONH— attached to pyrrole (N-CH₃)—benzimidazole (NH)—CONH—phenyl(R₃)—N(CH₂CH₂Cl)₂, with counterion X⁻]

| No. | X⁻ | R₁ | R₂ | R₃ | m |
|---|---|---|---|---|---|
| 45 | CH₃—C₆H₄—SO₃⁻ | CH₃CH₂CH₂ | CH₃CH₂CH₂ | H | 2 |
| 46 | CH₃—C₆H₄—SO₃⁻ | CH₃CH₂CH₂ | CH₃CH₂CH₂ | CH₃ | 2 |
| 47 | CH₃—C₆H₄—SO₃⁻ | CH₃CH₂CH₂ | CH₃CH₂CH₂ | Cl | 2 |
| 48 | CH₃—C₆H₄—SO₃⁻ | CH₃CH₂CH₂ | CH₃CH₂CH₂ | OCH₃ | 2 |
| 49 | CH₃SO₃⁻ | CH₃CH₂ | CH₃CH₂ | H | 1 |
| 50 | CH₃SO₃⁻ | CH₃CH₂ | CH₃CH₂ | CH₃ | 1 |
| 51 | CH₃SO₃⁻ | CH₃CH₂ | CH₃CH₂ | H | 3 |
| 52 | CH₃SO₃⁻ | CH₃CH₂ | CH₃CH₂ | CH₃ | 3 |
| 53 | CH₃SO₃⁻ | CH₃CH₂ | CH₃CH₂CH₂ | H | 1 |
| 54 | CH₃SO₃⁻ | CH₃CH₂ | CH₃CH₂CH₂ | CH₃ | 1 |
| 55 | CH₃SO₃⁻ | CH₃CH₂ | CH₃CH₂CH₂ | H | 3 |
| 56 | CH₃SO₃⁻ | CH₃CH₂ | CH₃CH₂CH₂ | CH₃ | 3 |
| 57 | CH₃SO₃⁻ | CH₃CH₂CH₂ | CH₃CH₂CH₂ | H | 1 |
| 58 | CH₃SO₃⁻ | CH₃CH₂CH₂ | CH₃CH₂CH₂ | CH₃ | 1 |
| 59 | CH₃SO₃⁻ | CH₃CH₂CH₂ | CH₃CH₂CH₂ | H | 3 |
| 60 | CH₃SO₃⁻ | CH₃CH₂CH₂ | CH₃CH₂CH₂ | CH₃ | 3 |
| 61 | CH₃—C₆H₄—SO₃⁻ | CH₃CH₂ | CH₃CH₂ | H | 1 |
| 62 | CH₃—C₆H₄—SO₃⁻ | CH₃CH₂ | CH₃CH₂ | CH₃ | 1 |
| 63 | CH₃—C₆H₄—SO₃⁻ | CH₃CH₂ | CH₃CH₂ | H | 3 |
| 64 | CH₃—C₆H₄—SO₃⁻ | CH₃CH₂ | CH₃CH₂ | CH₃ | 3 |
| 65 | CH₃—C₆H₄—SO₃⁻ | CH₃CH₂ | CH₃CH₂CH₂ | H | 1 |
| 66 | CH₃—C₆H₄—SO₃⁻ | CH₃CH₂ | CH₃CH₂CH₂ | CH₃ | 1 |

TABLE 1-continued

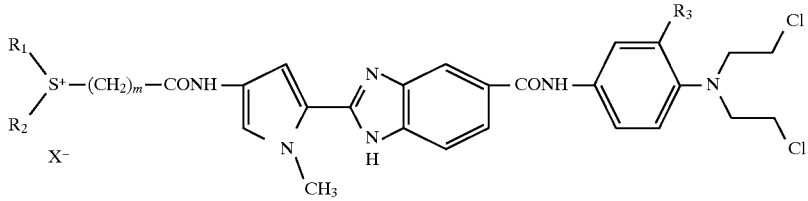

| No. | X⁻ | R₁ | R₂ | R₃ | m |
|---|---|---|---|---|---|
| 67 | CH₃—⟨benzene⟩—SO₃⁻ | $CH_3CH_2$ | $CH_3CH_2CH_2$ | H | 3 |
| 68 | CH₃—⟨benzene⟩—SO₃⁻ | $CH_3CH_2$ | $CH_3CH_2CH_2$ | $CH_3$ | 3 |
| 69 | CH₃—⟨benzene⟩—SO₃⁻ | $CH_3CH_2CH_2$ | $CH_3CH_2CH_2$ | H | 1 |
| 70 | CH₃—⟨benzene⟩—SO₃⁻ | $CH_3CH_2CH_2$ | $CH_3CH_2CH_2$ | $CH_3$ | 1 |
| 71 | CH₃—⟨benzene⟩—SO₃⁻ | $CH_3CH_2CH_2$ | $CH_3CH_2CH_2$ | H | 3 |
| 72 | CH₃—⟨benzene⟩—SO₃⁻ | $CH_3CH_2CH_2$ | $CH_3CH_2CH_2$ | $CH_3$ | 3 |

The compounds of the present invention can be used as antitumor agents having an excellent activity. Applicable carcinomas are leukemia, osteosarcoma, breast carcinoma, ovarian carcinoma, stomach carcinoma, colon carcinoma, lung carcinoma, head and neck carcinoma or the like.

Pharmaceutical preparations can be produced by known methods. Various forms of preparations can be selected depending on the purposes of the treatment. Representative forms are, for example, solid preparations, liquid preparations and other preparations such as suppositories. More specifically, various forms of preparations are, for example, tablets, pills, dispersible powders, granules, capsules for solid preparations; injectable solutions, suspensions, syrups, emulsions for liquid preparations; and suppositories for other preparations.

In preparing tablet form preparations, various kinds of vehicles which are conventionally known in the art can be widely used. For example, they are excipients such as lactose, sucrose, sodium chloride, glucose, starch, calcium carbonate, kaolin, crystalline cellulose and silicic acid; bonding agents such as water, ethanol, propanol, simple syrup, glucose solution, starch solution, gelatin solution, shellac solution, methyl cellulose solution, hydroxypropyl cellulose solution, polyvinylpyrrolidone solution and carboxymethyl cellulose solution; disintegrating agents such as dry starch, sodium alginate, agar powder, sodium hydrogencarbonate, calcium carbonate, polyoxyethylene-sorbitan fatty acid esters, sodium lauryl sulfate, stearic acid monoglycerides, starch and lactose; disintegration suppressing agents such as sucrose, stearic acid, cacao butter and hydrogenated oils; absorption promoting agents such as quaternary ammonium bases and sodium lauryl sulfate; moisture retaining agents such as glycerol and starch; absorbing agents such as starch, lactose, kaolin, bentonite, colloidal silicic acid, crystalline cellulose and light silicic acid anhydride; or lubricating agents such as talc, stearate, boric acid powder and polyethylene glycol.

Further, in preparation of tablets, if appropriate, tablets coated with customary coating agents, such as sugar-coated tablets, gelatin-coated tablets, enteric coated tablets and film-coated tablets can be prepared. Double-layered or multiple-layered tablets can also be prepared.

In preparation of pills, vehicles which are known in the art can be generally used. Examples of such vehicles include excipients such as glucose, lactose, starch, cacao butter, hydrogenated vegetable oils, kaolin and talc; bonding agents such as acacia gum powder, tragacanth gum powder and gelatin; and disintegrating agents such as calcium calmerose and agar.

Capsule preparations can be prepared generally by mixing effective compounds with various vehicles as mentioned above and dispensing the mixture into hard gelatine capsules or soft gelatin capsules, according to the customary method.

In preparation of injectable preparations in forms of solutions, emulsions and suspensions, diluents which are generally used in the art can be known. Examples of such diluents include water, ethanol, macrogol, propylene glycol, ethoxylated isostearyl alcohol, polyoxylated isostearyl alcohol, polyoxyethylene sorbitan fatty acid esters, cotton seed oil, corn oil, peanut oil and olive oil. Furthermore, injectable preparations can be prepared by adding water to compositions of the present invention in the presence of appropriate surface active agents to produce aqueous suspensions. Further, injectable emulsions can be prepared using surface active agents such as polyoxyethylene hydrogenated castor oil (HCO-60), polysorbate 80 and polyethylene glycol. Further, table salt, glucose or glycerol may be contained in the pharmaceutical preparations, and customary solution promoting agents, buffering agents, pain-relieving agents or the like can be also added to the preparations.

In preparation of suppositories, vehicles which are conventionally known can be generally used. Examples of such vehicles include polyethylene glycol, cacao butter, higher alcohols, esters of higher alcohols, gelatin and semi-synthetic glycerides.

Furthermore, if appropriate, coloring agents, preserving agents, perfumes, flavoring agents, sweetening agents or the like and other medicinal agents can be included in the above-mentioned pharmaceutical preparations.

Methods of administrating these pharmaceutical preparations are not specifically restricted. The preparations can be administered depending on the forms of preparations, age, sex and other conditions of patients, severity of the disease to be treated. For example, preparations are orally administered in the cases of tablets, pills, liquid agents, suspensions, emulsions, dispersible powders, granules, syrups or capsule preparations. Injectable solutions are intravenously injected singularly or as an admixture with a customary adjunct fluid such as glucose or amino acids; or, if appropriate, they are singularly injected intramuscularly, subcutaneously or intraperitoneally. Suppositories are applied to the rectum. Doses of the preparations are appropriately selected depending on mode of administration, age, sex or other conditions of patients and severity of the disease to be treated; however, in general, it is preferable to administer effective compounds in a daily dose of between about 0.001 and 1,000 mg for an adult. Furthermore, it is desirable that effective compounds are contained in pharmaceutical compounds in a range between about 0.001 and 1,000 mg per dose unit.

Generally speaking, antitumor agents, for example, even generally used drugs such as adriamycin or cisplatin, are not a kind of drug whose side effects are small. Viewing from a level of today's technology, side-effects have to be judged by taking relations with strength of action into considerations and are not avoidable to some extent. Side effects of compounds of the present invention are considered to be at acceptable level for usage for antitumor agents.

The present invention will be explained by the following Reference Example, Examples and Test Examples; however, the invention is not intended to be limited to these examples.

Reference Example 1

I. N,N-Bis(2-chloroethyl)-1,4-phenylenediamine hydrochloride

4-Nitro-[N,N-bis(2-chloroethyl)]aniline (5.0 g; 19.0 mmol) was dissolved in a mixed solvent of 50 ml of ethyl acetate and 25 ml of methanol, followed by the addition of 5.0 ml of 4N hydrochloric acid. Using 10% Pd/C, the reactant was subjected to hydrogenation under normal pressure at room temperature. The Pd/C was filtered off and the solvent was distilled out. The residue was crystallized from ethanol-ethyl ether, whereby 4.1 g (15.2 mmol) of the title compound was obtained (yield: 80%). m.p. 230°–233° C.

II. 1H-2-(1-Methyl-4-nitropyrrol-2-yl)benzimidazole-5-[N-[4-[N,N-bis(2-chloroethyl)amino]phenyl]]carboxamide 1H-2-(1-Methyl-4-nitropyrrol-2-yl)benzimidazole-5-carboxylic acid (0.3 g; 1.05 mmol) was dissolved-in 6 ml of DMF, to which a solution of 0.3 g (1.1 mmol; 1.05 equivalents) of N,N-bis(2-chloroethyl)-1,4-phenylenediamine hydrochloride and 0.15 ml (1.82 mmol; 3.1 equivalents) of triethylamine in 8 ml of DMF was added dropwise. Added next was 0.16 g (1.18 mmol; 1.1 equivalents) of HOBt. The resulting mixture was ice-cooled under a nitrogen gas atmosphere, followed by the addition of 0.24 g (1.16 mmol; 1.1 equivalents) of DCC. The temperature of the resulting mixture was allowed to rise again to room temperature, at which the mixture was stirred for 3 hours and was then allowed to stand overnight. The resulting solid was filtered off and the filtrate was concentrated under reduced pressure. The residue was purified by chromatography on a silica gel column (methylene chloride/2% methanol). The reaction product was washed with methanol, whereby 0.38 g (0.76 mmol) of the title compound was obtained as yellow crystals (yield: 72.2%). m.p. 144°–148° C.

III. 1H-2-[1-Methyl-4-[3-(methylthio)propionylamino]pyrrol-2-yl]benzimidazole-5-[N-[4-[N,N-bis(2-chloroethyl)amino]phenyl]]carboxamide In a mixed solvent of 3 ml of DMF and 3 ml of methanol, 0.20 g (0.40 mmol) of 1H-2-(1-methyl-4-nitropyrrol-2-yl)benzimidazole-5-[N-[4-[N,N-bis(2-chloroethyl)amino]phenyl]]carboxamide was dissolved, followed by the addition of 0.45 ml of 1N hydrochloric acid. Using 0.10 g of 10% Pd/C (wet) as a catalyst, hydrogenation was conducted under normal pressure to obtain the corresponding amino derivative. A solution of the amino derivative in DMF was stirred under a nitrogen gas stream and ice cooling. To the reaction mixture, 67 $\mu$l (0.48 mmol; 1.2 equivalents) of triethylamine and a DMF solution of 3-(methylthio)-propionylimidazole, which had been prepared by dissolving 0.06 g (0.50 mmol; 1.2 equivalents) of 3-(methylthio) propionic acid and 95 mg (0.59 mmol; 1.4 equivalents) of CDI in 3 ml of DMF, were added. The temperature of the resultant mixture was allowed to rise back to room temperature, at which the mixture was stirred for 4 hours. The reaction mixture was then allowed to stand overnight, followed by concentration under reduced pressure. The residue was purified by chromatography on a silica gel column (chloroform/4% methanol) and crystallized from ethyl acetate-ethyl ether, whereby 164 mg (0.29 mmol) of the title compound were obtained as light brown crystals (yield: 71.6%).

IR(KBr)cm$^{-1}$: 3275, 1642, 1518, 1327, 813

Elemental analysis for $C_{27}H_{30}Cl_2N_6O_2S$: Calculated: C 56.54; H 5.22; N 14.30; Cl 12.30 Found: C 56.12; H 5.22; N 14.30; Cl 12.30

EXAMPLE 1

(Compound Number 25)

2-[N-[1-Methyl-2-[5-[N-[4-[N,N-bis(2-chloroethyl)amino]phenyl]]carbamoyl]-1H-benzimidazol-2-yl]pyrrol-4-yl]carbamoylethyl-dimethylsulfonium p-toluenesulfonate 1H-2-[1-Methyl-4-(3-methylthiopropionyl)aminopyrrol-2-yl]benzimidazole-5-[N-[4-[N,N-bis(2-chloroethyl)amino]phenyl]]carboxamide (0.2 g) was dissolved in 2 ml of 98–100% formic acid. To this solution was added 2 ml of methyl p-toluenesulfonic acid, and the mixture was stirred at room temperature for 2 hours in darkness and then allowed to stand overnight. The reaction solution was diluted with methanol and the solvent was distilled out under reduced pressure. The residue was purified by chromatography on a gel filtration column (Sephadex LH-20, methanol) and was further treated with ethyl ether, whereby 0.21 g (86%) of the title compound was obtained as a yellow powder.

Analysis of the title compound obtained:
NMR analysis
NMR (DMSO-$d_6$) δ: 10.31 (s, 1H), 10.02 (s, 0.4H), 9.96 (s, 0.6H), 8.32 (s, 0.6H), 8.02 (s, 0.4H), 7.81 (m, 1.5H), 7.64 (m, 3H), 7.52 (d, 0.5H), 7.48 (d, 2H), 7.47 (s, 1H), 7.11 (d, 2H), 6.95 (d, 1H), 6.76 (d, 2H), 4.09 (s, 3H), 3.73 (s, 8H), 3.53 (t, 2H), 2.94 (s, 6H), 2.93 (t, 2H), 2.29 (s, 3H).

Elemental analysis for $C_{35}H_{36}N_6O_5Cl_2S_2 \cdot 2H_2O$ Calculated: C 53.09; H 5.09; N 10.61 Analyzed: C 53.20; H 5.27; N 10.37

EXAMPLE 2

(Compound Number 1)
2-[N-[1-Methyl-2-[5-[N-[4-[N,N-bis(2-chloroethyl)amino]phenyl]]carbamoyl]-1H-benzimidazol-2-yl]pyrrol-4-yl]carbamoylethyl-dimethylsulfonium methanesulfonate 1H-2-[1-Methyl-4-(3-methylthiopropionyl)aminopyrrol-2-yl]benzimidazole-5-[N-[4-[N,N-bis(2-chloroethyl)amino]phenyl]]carboxamide (0.3 g) was dissolved in 3 ml of 98–100% formic acid. To this solution was added 3 ml of methyl methanesulfonate, and the mixture was stirred at room temperature for 9 hours in darkness and then allowed to stand overnight. The reaction solution was diluted with methanol and the solvent was distilled out under reduced pressure. IPE was added, the admixture was stirred, and IPE was removed by decantation. Ethyl ether was added to the resulting residue, the admixture was stirred, and ethyl ether was removed by decantation. The resulting residue was treated with ethyl ether, whereby 0.33 g (97%) of the title compound was obtained as a yellow powder.

Analysis of the title compound obtained:
NMR analysis
NMR (DMSO-$d_6$) δ:10.33 (s, 1H), 9.99 (s, 1H), 8.15 (s, 1H), 7.81 (d, 1H), 7.65 (d, 2H), 7.60 (bs, 1H), 7.30 (s, 1H), 6.95 (s, 1H), 6.77 (d, 2H), 4.10 (s, 3H), 3.73 (s, 8H), 3.54 (t, 2H), 2.95 (s, 6H), 2.94 (t, 2H), 2.34 (s, 3H).

Elemental analysis for $C_{29}H_{36}N_6O_5Cl_2S_2 \cdot 2H_2O$ Calculated: C 48.40; H 5.60; N 11.68 Analyzed: C 48.48; H 5.07; N 11.11

EXAMPLE 3

(Compound Number 25, p-toluenesulfonate)
2-[N-[1-Methyl-2-[5-[N-[4-[N,N-bis(2-chloroethyl)amino]phenyl]]carbamoyl]-1H-benzimidazol-2-yl]pyrrol-4-yl]carbamoylethyl-dimethylsulfonium p-toluenesulfonate, p-toluenesulfonate 1H-2-[1-Methyl-4-(3-methylthiopropionyl)aminopyrrol-2-yl]benzimidazole-5-[N-[4-[N,N-bis(2-chloroethyl)amino]phenyl]]carboxamide (10.1 g) was dissolved in 35 ml of 98–100% formic acid. To this solution were added 8 ml of methyl p-toluenesulfonic acid and 4.1 g (1.2 equivalents) of p-toluenesulfonic acid monohydrate, and then the mixture was stirred at room temperature for 2 days in darkness. Treatment with ethyl acetate and decantation were repeated 2 times each (700 ml×2), and then sludging was carried out with 300 ml of ethyl acetate to obtain a light yellow powder. This was purified by chromatography on a gel filtration column (Sephadex LH-20, methanol) and was recrystallized from methanol, whereby 8.72 g (53%) of the title compound were obtained.

Analysis of the title compound obtained:
NMR analysis
NMR (DMSO-$d_6$) δ: 10.38 (s, 1H), 10.12 (s, 1H), 8.23 (s, 1H), 7.95 (d, 1H), 7.71 (d, 1H), 7.64 (d, 2H), 7.48 (d, 4H), 7.42 (s, 1H), 7.15 (d, 4H), 7.07 (s, 1H), 6.77 (d, 1H), 4.06 (s, 3H), 3.74 (s, 8H), 3.54 (t, 2H), 2.94 (s, 6H), 2.94 (t, 2H), 2.29 (s, 6H).

Elemental analysis for $C_{42}H_{48}N_6O_8Cl_2S_3 \cdot H_2O$ Calculated: C 53.10; H 5.30; N 8.85 Analyzed: C 53.01; H 5.20; N 8.56

EXAMPLE 4

(Compound Number 25, methanesulfonate)
2-[N-[1-Methyl-2-[5-[N-[4-[N,N-bis(2-chloroethyl)amino]phenyl]]carbamoyl]-1H-benzimidazol-2-yl]pyrrol-4-yl]carbamoylethyl-dimethylsulfonium p-toluenesulfonate, methanesulfonate 1H-2-[1-Methyl-4-(3-methylthiopropionyl)aminopyrrol-2-yl]benzimidazole-5-[N-[4-[N,N-bis(2-chloroethyl)amino]phenyl]]carboxamide (0.1 g) was dissolved in 1 ml of 98–100% formic acid. To this solution were added 1 ml of methyl p-toluenesulfonate and 12 μl (1.1 equivalents) of methanesulfonic acid, and the mixture was stirred at room temperature for 2 hours in darkness and then allowed to stand overnight. The reaction solution was diluted with methanol, and the resulting solution was purified by chromatography on a gel filtration column (Sephadex LH-20, methanol) and was further treated with ethyl ether, whereby 0.08 g (54%) of the title compound was obtained as a yellow powder.

Analysis of the title compound obtained:
NMR analysis
NMR (DMSO-$d_6$) δ: 10.40 (s, 1H), 10.13 (s, 1H), 8.24 (s, 1H), 7.96 (d, 1H), 7.73 (d, 1H), 7.64 (d, 2H), 7.48 (d, 2H); 7.44 (s, 1H), 7.13 (s, 1H), 7.09 (d, 2H), 6.77 (d, 2H), 4.06 (s, 3H), 3.74 (s, 8H), 3.54 (t, 2H), 2.95 (s, 6H), 2.95 (t, 2H), 2.35 (s, 3H), 2.29 (s, 3H).

EXAMPLE 5

(Compound Number 1, methanesulfonate)
2-[N-[1-Methyl-2-[5-[N-[4-[N,N-bis(2-chloroethyl)amino]phenyl]]carbamoyl]-1H-benzimidazol-2-yl]pyrrol-4-yl]carbamoylethyl-dimethylsulfoniummethanesulfonate, methanesulfonate 1H-2-[1-Methyl-4-(3-methylthiopropionyl)-aminopyrrol-2-yl]benzimidazole-5-[N-[4-[N,N-bis(2-chloroethyl)amino]phenyl]]carboxamide (8.1 g) was dissolved in 20 ml of 98–100% formic acid. To this solution were added 3.58 ml (42.3 mmol) of methyl methanesulfonic acid and 1.1 ml (17.0 mmol) of methanesulfonic acid, and then the mixture was stirred at room temperature for 32 hours in darkness. The reaction solution was subjected twice to the treatment with ethyl ether and decantation, the resulting residue was purified by chromatography on a gel filtration column (Sephadex LH-20, methanol), and the purified product was further treated with ethyl ether, whereby 8.0 g (73%) of the title compound were obtained as a yellow powder.

Analysis of the title compound obtained:
NMR analysis
NMR (DMSO-$d_6$) δ: 10.45 (s, 1H), 10.16 (s, 1H), 8.26 (s, 1H), 8.00 (d, 1H), 7.77 (d, 2H), 7.64 (d, 2H), 7.49 (s, 1H), 7.12 (s, 1H), 6.77 (d, 2H), 4.06 (s, 3H), 3.74 (s, 8H), 3.55 (t, 2H), 2.95 (s, 6H), 2.95 (t, 2H), 2.38 (s, 6H).

Elemental analysis $C_{30}H_{40}N_6O_8Cl_2S_3 \cdot H2O$ Calculated: C 45.17; H 5.31; N 10.53 Analyzed: C 45.10; H 5.08; N 10.27

EXAMPLE 6

The following compound was synthesized as described in Examples 1 to 5.

2-[N-[1-Methyl-2-[5-[N-[4-[N,N-bis(2-chloroethyl)amino]phenyl]]carbamoyl]-1H-benzimidazol-2-yl]pyrrol-4-yl]carbamoylethyl-dimethylsulfonium trifluoromethanesulfonate Analysis of the target compound obtained:

NMR analysis

NMR (DMSO-$d_6$) δ:10.31 (s, 1H), 9.98 (s, 1H), 8.22 (s, 1H), 7.81 (d, 1H), 7.64 (d, 2H), 7.57 (bd, 2H), 7.29 (s, 1H), 6.95 (s, 1H), 6.76 (d, 2H), 4.09 (s, 3H), 3.73 (s, 8H), 3.54 (t, 2H), 2.94 (s, 6H), 2.93 (t, 2H).

Elemental analysis for $C_{29}H_{32}N_6O_5Cl_2F_3S_2 \cdot 0.5H_2O$ Calculated: C 46.71; H 4.46; N 11.27 Analyzed: C 46.92; H 4.57; N 10.98

EXAMPLE 7

The following compound was synthesized as described in Examples 1 to 5.

2-[N-[1-Methyl-2-[5-[N-[4-[N,N-bis(2-chloroethyl)amino]phenyl]]carbamoyl]-1H-benzimidazol-2-yl]pyrrol-4-yl]carbamoylethyl-dimethylsulfonium trifluoromethanesulfonate, trifluoromethanesulfonate, Analysis of the target compound obtained:

NMR analysis

NMR (DMSO-$d_6$) δ: 10.37 (s, 1H), 10.12 (s, 1H), 8.23 (s, 1H), 7.95 (d, 1H), 7.71 (d, 2H), 7.63 (d, 2H), 7.42 (s, 1H), 7.07 (s, 1H), 6.77 (d, 2H), 4.07 (s, 3H), 3.74 (s, 8H), 3.53 (t, 2H), 2.94 (s, 6H), 2.94 (t, 2H).

Elemental analysis for $C_{30}H_{33}N_6O_8Cl_2F_6S_3 \cdot H_2O$ Calculated: C 39.83; H 3.90; N 9.29 Analyzed: C 39.74; H 4.03; N 9.03

EXAMPLE 8

1H-2-[1-Methyl-4-(3-methylthiopropionyl)aminopyrrol-2-yl]benzimidazole-5-[N-[4-[N,N-bis(2-chloroethyl)amino]phenyl]]carboxamide, methanesulfonate 1H-2-[1-Methyl-4-(3-methylthiopropionyl)aminopyrrol-2-yl]benzimidazole-5-[N-[4-[N,N-bis(2-chloroethyl)amino]phenyl]]carboxamide (570 mg) was dissolved in methanol, and 2 equivalents by mole of methanesulfonic acid, which was separately prepared, was added dropwise to the solution. After stirring for 30 minutes, resulting yellow needle-like crystals were filtered and dried, whereby 597 mg of the title compound were obtained.

NMR analysis

NMR (DMSO-$d_6$) δ: 10.15 (s, 1H), 10.12 (s, 1H), 8.24 (s, 1H), 7.97 (d, 1H), 7.74 (d, 2H), 7.63 (d, 2H), 7.45 (s, 1H), 7.08 (s, 1H), 6.78 (d, 2H), 4.05 (s, 3H), 3.74 (s, 8H), 2.76 (t, 2H), 2.58 (t, 2H), 2.34 (s, 3H), 2.09 (s, 3H).

EXAMPLE 9

1H-2-[1-Methyl-4-(3-methylthiopropionyl)aminopyrrol-2-yl]benzimidazole-5-[N-[4-[N,N-bis(2-chloroethyl)amino]phenyl]]carboxamide, p-toluenesulfonate This p-Toluenesulfonate compound was obtained as described in Example 8.

NMR analysis

NMR (DMSO-$d_6$) δ: 10.15 (s, 1H), 10.11 (s, 1H), 8.23 (s, 1H), 7.98 (d, 1H), 7.73 (d, 1H), 7.63 (d, 2H), 7.48 (d, 4H), 7.45 (s, 1H), 7.11 (d, 4H), 6.77 (d. 2H), 4.04 (s, 3H), 3.74 (s, 8H), 2.76 (t, 2H), 2.58 (t, 2H), 2.35 (s, 3H), 2.09 (s, 6H).

Formulation Example 1

| | |
|---|---|
| Compound No. 25 as an active ingredient | 30 g |
| Lactose | 68 g |
| Crystalline cellulose | 20 g |
| Magnesium stearate | 2 g |

The components described above were mixed in the above composition and the resulting mixture was formulated into core tablets by a tableting machine. Each of the core tablets weighed 120 mg containing 30 mg of Compound No. 25 and had a diameter of 7 mm.

Talc was then sprinkled on each core tablet and the surface having talc was then coated with varnish to form an undercoat. Additional varnish coating was repeated so as to obtain tablets suitable for internal uses. Color coating was further conducted. After drying, the tablets having the color coats were waxed and polished into tablets of uniform gloss.

Formulation Example 2

As an active ingredient, 1 g of Compound No. 25 was weighed and dissolved in 1,000 ml of sterilized propylene glycol. The resting solution was poured and enclosed in ampoules so as to obtain injections in ampoules, each of which contained 5 ml of the solution.

Test Example 1

(In Vitro Tumor Cell Growth Suppressing Activity)

Antitumor activity of the above-mentioned compounds was tested as follows. Mouse B16 melanoma cells were plated on a 96-well culture plate, test compounds were added to the cells one day after, and then the plate was incubated at 37° C. for 3 days under a 5%-$CO_2$ atmosphere. According to the method described in Cancer Res. 48, 589–601, 1988, the concentrations of compounds required to inhibit cell growth by 50% were obtained. Antitumor activities of representative compounds are shown in Table 2. The activity is expressed by the concentrations (micrograms/milliliter). The result with distamycin is also shown for comparison.

TABLE 2

| In vitro tumor cell growth suppressing activity | |
|---|---|
| Compound Number | 50% Suppressing Concentration (μg/ml) |
| 1 | 1.12 |
| 1*[1] | 0.71 |
| 25*[2] | 0.99 |
| Distamycin | 36.0 |

Note:
*[1]Methanesulfonate
*[2]p-toluenesulfonate

Test Example 2

A cell suspension of Colon 26 mouse colon cancer cells ($1\times10^7$ cells/ml) in HBSS (Hanks' Balanced Salt Solution) was prepared. This cell suspension (0.1 ml each) was implanted subcutaneously into the lateral region of female CDF1 mice (day 0). One day after the tumor cell injection (day 1), the body weight of the mice was measured, and then solutions of test compounds (5% glucose solutions containing 5% Tween 80) were injected intravenously into the tails of the mice. On day 15, the resulting tumors were taken out and weighed.

Percent average weights of tumors of animals in the test groups, in which the compounds were injected, with respect to those in the control group, in which no compounds were injected, were calculated and given as T/C values. Concentrations of the compounds which gave 50% T/C values are shown in Table 3.

TABLE 3

In vivo antitumor activity

| Compound Number | 50% T/C (mg/kg) |
|---|---|
| 1*1 | 7.19 |
| 25*2 | 9.35 |
| Adriamycin | 12.4 |

Note:
*1Methanesulfonate;
*2p-toluenesulfonate

Test Example 3

In order to compare stabilities of the compounds, remaining rates of compounds were obtained by incubating the compounds at about 4° C. and 50° C. for 3 days and measuring comparative peak areas on HPLC (Table 4).

TABLE 4

Stability of compounds (1)

| Compound | Temperature | Remaining rate |
|---|---|---|
| 1*1 | 50° C. | 100% |
| IODIDE | 50° C. | 83% |
| IODIDE | 4° C. | 99% |

Note:
*1Methansulfonate
*IODIDE: Counteranion of Compound 1 was changed into iodide, and other salts were not involved in the compound.

Test Example 4

Stability of these compounds was investigated. As an index of stability, remaining rates of compounds were obtained by measuring remaining compounds after heating at 60° C. for one month. The remaining rates were measured by HPLC. Results are shown in Table 5.

TABLE 5

Stability of compounds (2)

| Compound | Remaining rate |
|---|---|
| 1*1 | 96.7% |
| 25*2 | 99.4% |

Note:
*1Methanesulfonate;
*2p-toluenesulfonate

What is claimed is:
1. A compound of formula (1):

$$\begin{array}{c} R_1 \\ \diagdown \\ S^+ - (CH_2)_m - CONH - \cdots \\ \diagup \\ R_2 \quad X^- \end{array} \quad (1)$$

wherein
m is an integer 1, 2 or 3,
$R_1$ and $R_2$ are the same or independently different alkyl groups, each having 1–5 carbon atoms,
$R_3$ is a hydrogen atom, alkyl group having 1–3 carbon atoms, alkoxy group having 1–3 carbon atoms or halogen atom, and
X is an acid radical of an acid selected from a group consisting of methanesulfonic acid, benzenesulfonic acid, toluenesulfonic acid and trifluoromethanesulfonic acid, or salt thereof.

2. The compound or salt thereof according to claim 1 wherein $R_3$ represents a hydrogen atom, methyl group, methoxy group or chlorine atom.

3. The compound or salt thereof according to claim 2 wherein both $R_1$ and $R_2$ are a methyl group.

4. 2-[N-[1-Methyl-2-[5-[N-[4-[N,N-bis(2-chloroethyl)amino]phenyl]]carbamoyl]-1H-benzimidazol-2-yl]pyrrol-4-yl]carbamoylethyl-dimethylsulfonium-p-toluenesulfonate or salts thereof.

5. 2-[N-[1-Methyl-2-[5-[N-[4-[N,N-bis(2-chloroethyl)amino]phenyl]]carbamoyl]-1H-benzimidazol-2-yl]pyrrol-4-yl]carbamoylethyl-dimethylsulfonium-methanesulfonate or salts thereof.

6. An antitumor agent comprising an effective amount of the compounds according to claim 5 as an effective compound.

7. An antitumor agent comprising an effective amount of the compounds according to claim 4 as an effective compound.

8. An antitumor agent comprising an effective amount of the compounds according to claim 3 as an effective compound.

9. An antitumor agent comprising an effective amount of the compounds according to claim 2 as an effective compound.

10. An antitumor agent comprising an effective amount of the compounds according to claim 1 as an effective compound.

* * * * *